United States Patent [19]

Oeckl et al.

[11] 4,230,723
[45] Oct. 28, 1980

[54] COMBATING PLANT BACTERIA WITH ACYLHALOGENOMETHYL THIOCYANATES

[75] Inventors: Siegfried Oeckl, Cologne; Hans Scheinpflug, Leverkusen; Peter Kraus, Cologne, all of Fed. Rep. of Germany

[73] Assignee: Bayer Aktiengesellschaft, Leverkusen, Fed. Rep. of Germany

[21] Appl. No.: 37,627

[22] Filed: May 10, 1979

[30] Foreign Application Priority Data

May 30, 1978 [DE] Fed. Rep. of Germany ....... 2823658

[51] Int. Cl.² .............................................. A01N 9/18
[52] U.S. Cl. ..................................................... 424/302
[58] Field of Search ........................................... 424/302

[56] References Cited

U.S. PATENT DOCUMENTS

| 2,923,658 | 2/1960 | Regel et al. ........................... 424/302 |
| 3,097,130 | 7/1963 | Regel et al. ........................... 424/302 |
| 3,366,538 | 1/1968 | Werres et al. ......................... 424/302 |
| 3,959,330 | 5/1976 | Phillips et al. ........................ 424/302 |

FOREIGN PATENT DOCUMENTS

| 42-118 | 7/1967 | Japan ...................................... 424/302 |
| 2339109 | 2/1975 | Fed. Rep. of Germany ........... 424/302 |
| 1450300 | 9/1976 | United Kingdom .................... 424/302 |

Primary Examiner—Douglas W. Robinson
Attorney, Agent, or Firm—Sprung, Felfe, Horn, Lynch & Kramer

[57] ABSTRACT

A method of combating bacteria comprising applying to the bacteria, or to a habitat thereof, an acylhalogenomethyl thiocyanate of the formula

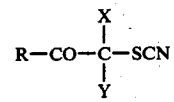

in which
R is alkyl with up to 6 carbon atoms, thienyl, phenyl, naphthyl, or phenyl substituted by halogen, hydroxy, alkyl with 1 to 4 carbon atoms, alkoxy with up to 4 carbon atoms, nitro or phenyl,
X is halogen, and
Y is halogen or hydrogen.

8 Claims, No Drawings

COMBATING PLANT BACTERIA WITH ACYLHALOGENOMETHYL THIOCYANATES

The present invention relates to the use of certain known acylhalogenomethyl thiocyanates for combating bacteria which are harmful to plants.

Plant diseases caused by pathogenic bacteria are becoming increasingly more widespread, so that now the value of cultivating some crop plants is already endangered economically in certain regions. Important pathogens belong to the Pseudomonadaceae family, for example *Pseudomonas solanacearum, Pseudomonas lachrymans, Pseudomonas syringae, Xanthomonas citri, Xanthomonas oryzae* and *Xanthomonas vesicatoria*, the Enterobacteriaceae family, for example *Erwinia amylovora*, or the Corynebacteriaceae family. The possible methods hitherto available for combating or preventing these diseases are very expensive and in addition still inadequate. In practice, antibiotics, the preparation of which is expensive and which frequently are toxic and, under atmospheric conditions, stable for only a short time, are generally used for this purpose. Furthermore, as has already been known for a long time, basic copper salts, for example copper oxychloride, or copper hydroxide/copper chloride mixtures can also be used for combating plant diseases (R. Wegler, Chemie der Pflanzenschutz-and Schädlingsbekämpfungsmittel (Chemistry of Plant Protection Agents and Agents for Combating Pests), Volume 2, Springer-Verlag, Heidelberg (1970). It is also known (see DE-OS (German Published Specification) No. 2,423,981) that acylhalogenomethyl thiocyanates display an activity against micro-organisms occurring in the industrial field, for example molds, yeasts, bacteria and slimes. They can therefore be used for preventing perishable goods and are recommended, above all, for preventing the growth of microbes in recycled industrial waters. Finally, "substituted dichloromethyl thiocyanates" are also proposed for combating nematodes, arachnidae, arthropods and insects, but above all for use as herbicides (U.S. Pat. No. 3,959,330).

It has now been found that the acylhalogenomethyl thiocyanates of the general formula

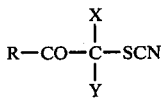

in which
R represents alkyl with up to 6 carbon atoms, the thienyl radical, phenyl (which is optionally substituted by halogen, hydroxy, alkyl with 1 to 4 carbon atoms, alkoxy with 1 to 4 carbon atoms, nitro or phenyl) or naphthyl, and
X and Y each represent halogen, provided that one of X and Y may alternatively represent hydrogen,
have a particularly good activity against bacteria which are harmful to plants.

Accordingly, the present invention provides a method for combating bacteria which comprises applying to the bacteria, or to a habitat thereof, a compound of the formula (I), alone or in admixture with a diluent or carrier.

Preferably, in formula (I), R represents alkyl with 1 to 4 carbon atoms, the thienyl radical, phenyl (which can be substituted by alkyl with 1 to 4 carbon atoms, methoxy, hydroxy, chlorine, bromine, nitro or phenyl) or naphthyl, and X and Y represent chlorine or bromine, provided that one of X and Y can alternatively represent hydrogen.

It is surprising that, in contrast to the dichloromethyl thiocyanates already known, the compounds which can be used according to the invention display no herbicidal action at all. This means, therefore, that no damage to plants is caused at all, and the use according to the invention for combating bacteria on plants becomes possible for the first time.

The compounds of the general formula (I) are known (see DE-OS (German Published Specification) No. 2,423,981 and British Pat. No. 1,450,300), as is their preparation from the corresponding acylmethyl thiocyanates by reaction with at least the stoichiometrically required amount of a halogen in the presence of an acid acceptor, in the temperature range between 0° and 100° C., preferably between 10° and 60° C.

Examples which may be mentioned of active compounds that can be used according to the invention are the α-chloro, α-bromo, α,α-dichloro and α,α-dibromo derivatives of the following acylmethyl thiocyanates: phenacyl thiocyanate, 4-nitro-phenacyl thiocyanate, 4-hydroxy-phenacyl thiocyanate, 4-methoxy-phenacyl thiocyanate, 4-isopropyl-phenacyl thiocyanate, 4-methyl-phenacyl thiocyanate, 4-ethyl-phenacyl thiocyanate, 4-chloro-phenacyl thiocyanate, 3,4-dichloro-phenacyl thiocyanate, 2,4,6-trichloro-3-methyl-phenacyl thiocyanate, thiocyanomethyl naphthyl ketone, thiocyanomethyl thienyl ketone and thiocyanopinacolin.

The active compounds according to the invention exhibit a powerful microbicidal action and can be employed in practice for combating undesired microorganisms. The active compounds are suitable for use as plant protection agents.

Bactericidal agents are employed in plant protection for combating Pseudomonoadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of the active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially for the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, especially 0.05 to 5 g, are generally employed per kilogram of seed.

For the treatment of soil, amounts of active compound of 0.00001 to 0.1% by weight, especially 0.0001 to 0.02%, are generally required at the place of action.

The compounds according to the invention have a particularly good activity against bacterial plant diseases.

These are caused by bacteria of the Pseudomonadaceae family, for example *Pseudomonas solanacearum, Pseudomonas lachrymans, Pseudomonas syringae, Pseudomonas morsprunorum, Pseudomonas phaseolicola, Pseudomonas tabaci, Xanthomonas oryzae, Xanthomonas citri, Xanthomonas campestris, Xanthomonas vesicatoria, Xanthomonas malvacearum, Xanthomonas translucens, Xanthomonas begoniae* and *Xanthomonas pelargonii,* of the Rhizobiaceae family, for example *Agrobacterium tumefaciens,* of the Enterobacteriaceae family, for example *Erwinia amylovora, Erwinia mangiferae* and *Erwinia carotovora,* of the Corynebacteriaceae family, for example *Corynebaceterium michiganense,* and of the Streptomycetaceae family, for example Streptomyces scabies.

In addition to the bactericidal action, the compounds according to the invention also exhibit an action against phytopathogenic fungi when applied in the appropriate amounts and concentrations. Fungicidal agents in plant protection are employed for combating Plasmodiophoromycetes, Oomycetes, Chytridiomycetes, Zygomycetes, Ascomycetes, Basidiomycetes and Deuteromycetes.

The compounds according to the invention exhibit, for example, a good action against cereal rust fungi (for example *Puccinia recondita*) and fungi of the genera Phytophthora, Fusarium and Verticillium.

In addition, the compounds according to the invention display an action against pests harmful to health, when applied in the appropriate amounts and concentrations.

The present invention further provides crops protected from damage by bacteria by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

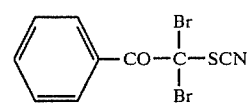 (1)

100 g (0.56 mol) of phenacyl thiocyanate and 154 g (1.12 mol) of sodium acetate were dissolved in 1 liter of glacial acetic acid. 179 g (1.12 mol) of bromine were added dropwise at 20° C., while stirring. When the addition was complete, the mixture was further warmed to 40° to 60° C. until the color had changed from red to light yellow. Sodium bromide was then filtered off, the solution was evaporated, the residue was stirred with water and the crystal mass was filtered off and dried. 182 g (96% of theory) of α,α-dibromophenacyl thiocyanate of melting point 98° C. were obtained.

Example 2

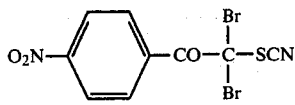

19 g (0.08 mol) of 4-nitro-phenacyl thiocyanate and 22 g (0.16 mol) of sodium acetate in 200 ml of glacial acetic acid were reacted with 27 g (0.16 mol) of bromine at 10° C. After the decoloration, the mixture was worked up analogously to Example 1. The yield was 26.6 g (94% of theory) of 4-nitro-α,α-dibromophenacyl thiocyanate of melting point 105° C.

Example 3

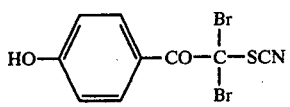

19.3 g (0.1 mol) of 4-hydroxy-phenacyl thiocyanate and 27 g (0.2 mol) of sodium acetate in 200 ml of glacial acetic acid were reacted with 32 g (0.2 mol) of bromine at 18° C. After removing sodium bromide and the solvent, the residue was stirred with water, whereupon a brown precipitate was formed, which, after filtering off, was recrystallized from ethanol. The yield was 12.4 g (32% of theory) of 4-hydroxy-α,α-dibromophenacyl thiocyanate of melting point 132° C.

Example 4

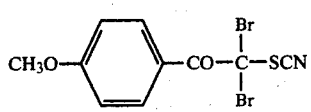

20.7 g (0.1 mol) of 4-methoxy-phenacyl thiocyanate and 27 g (0.2 mol) of sodium acetate were suspended in 200 ml of glacial acetic acid, and 32 g (0.2 mol) of bromine were added all at once. After stirring the mixture at 20° C. for 24 hours, sodium bromide was filtered off and the colorless filtrate was worked up in the customary manner. The yield was 53.2 g (91% of theory) of 4-methoxy-α,α-dibromophenacyl thiocyanate of melting point 40° C.

Example 5

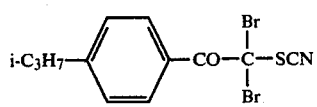

32 g (0.2 mol) of bromine were added to 22.3 g (0.1 mol) of 4-isopropyl-phenacyl thiocyanate and 27 g (0.2 mol) of sodium acetate in 200 ml of glacial acetic acid and the mixture was left to stand at 20° C. for 24 hours, whereupon decoloration occurred. The mixture was worked up in the customary manner. Yield: 26.5 g (70% of theory) of 4-isopropyl-α,α-dibromophenacyl thiocyanate of melting point 100° C.

Example 6

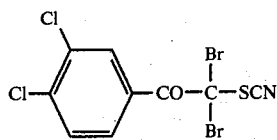

15 g (0.06 mol) of 3,4-dichlorophenacyl thiocyanate and 16.7 g (0.12 mol) of sodium acetate in 250 ml of glacial acetic acid were reacted with 19.6 g (0.12 mol) of bromine at 12° C. After decoloration, the mixture was worked up in the customary manner. Yield: 23.3 g (94% of theory) of 3,4-dichloro-α,α-dibromophenacyl thiocyanate of melting point 95° C.

Example 7

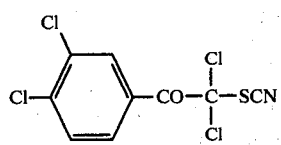

12.3 g (0.05 mol) of 3,4-dichloro-phenacyl thiocyanate and 7.7 g (0.1 mol) of ammonium acetate in 250 ml of glacial acetic acid were reacted with 7.0 g (0.1 mol) of chlorine. After decoloration, the mixture was concentrated directly and the residue was stirred with water. The crystals were recrystallized from ligroin. Yield: 13 g (84% of theory) of 3,4-dichloro-α,α-dichlorophenacyl thiocyanate of melting point 50° C.

Example 8

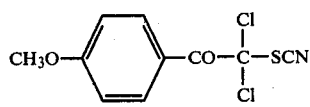

27.5 g (0.14 mol) of 4-nitro-phenacyl thiocyanate and 23 g (0.28 mol) of anhydrous sodium acetate in 170 ml of glacial acetic acid were reacted with 19.6 g (0.28 mol) of chlorine at a temperature of 25° to 30° C. After decoloration, the reaction mixture was worked up in the customary manner. 31.5 g (77% of theory) of 4-nitro-α,α-dichlorophenacyl thiocyanate of melting point 83-84° C. were obtained.

Example 9

20.7 g (0.1 mol) of 4-methoxy-phenacyl thiocyanate and 27 g (0.2 mol) of sodium acetate in 200 ml of glacial acetic acid were reacted with 14 g (0.2 mol) of chlorine at 30°-40° C. After decoloration, the reaction mixture was worked up in the customary manner. Yield: 20.6 g (75% of theory) of 4-methoxy-α,α-dichlorophenacyl thiocyanate of melting point 76°-80° C.

Example 10

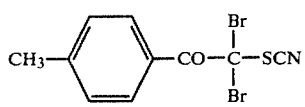
(10)

19 g (0.1 mol) of 4-methyl-phenacyl thiocyanate and 42 g (0.3 mol) of sodium acetate in 200 ml of glacial acetic acid were reacted with 16.8 g (0.12 mol) of chlorine at a temperature of 40°–50° C. After 5 hours, the mixture was worked up in the customary manner. Yield: 23 g (89% of theory) of 4-methyl-α,α-dichlorophenacyl thiocyanate of melting point 57° C.

Example 11

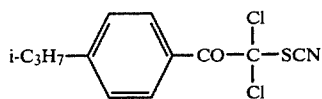
(11)

41 g (1.9 mol) of 4-isopropyl-phenacyl thiocyanate and 31.3 g (2.8 mol) of anhydrous sodium acetate in 150 ml of glacial acid were reacted with 26.6 g (0.4 mol) of chlorine at +15° C. After decoloration, the reaction mixture was worked up in the customary manner. Yield: 44.8 g (82% of theory) of 4-isopropyl-α,α-dichlorophenacyl thiocyanate of melting point 71°–73° C.

Example 12

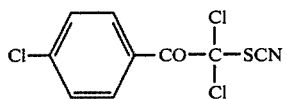
(12)

25 g (0.12 mol) of 4-chloro-phenacyl thiocyanate and 33 g (0.24 mol) of sodium acetate in 350 ml of glacial acetic acid were reacted with 16.8 g (0.24 mol) of chlorine in the temperature range between 20° and 30° C. After decoloration, the reaction mixture was worked up in the customary manner. Yield: 29.5 g (90% of theory) of 4-chloro-α,α-dichlorophenacyl thiocyanate of melting point 108° C.

Example 13

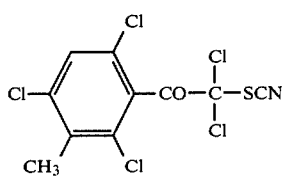
(13)

21 g (0.07 mol) of 2,4,6-trichloro-3-methyl-phenacyl thiocyanate and 11.7 g (0.14 mol) of anhydrous sodium acetate were reacted with 10.0 g (0.14 mol) of chlorine at 20° C. After decoloration, the mixture was worked up in the customary manner. Yield: 25 g (98% of theory) of 2,4,6-trichloro-3-methyl-α,α-dichlorophenacyl thiocyanate of melting point 70°–72° C.

Example 14

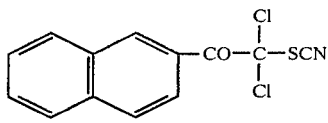
(14)

30 g (0.13 mol) of thiocyanomethyl β-naphthyl ketone and 35.8 g (0.26 mol) of sodium acetate in 300 ml of glacial acetic acid were reacted with 18.4 g (0.26 mol) of chlorine at +20° C. to 30° C. After decoloration, the mixture was worked up in the customary manner. Yield: 30.2 g (79% of theory) of thiocyano-dichloromethyl β-naphthyl ketone, a liquid with the refractive index $n_D^{20} = 1.6568$.

Example 15

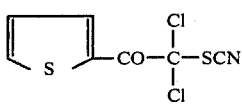
(15)

30 g (0.17 mol) of thiocyanomethyl thienyl ketone and 46 g (0.34 mol) of sodium acetate in 150 ml of glacial acetic acid were reacted with 24 g (0.34 mol) of chlorine at +15° C. to 20° C. After decoloration, the mixture was worked up in the customary manner. Yield: 30 g (71% of theory) of thiocyano-dichloromethyl thienyl ketone of melting point 75°–78° C.

Example 16

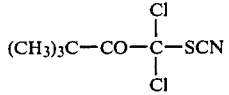
(16)

14.2 g (0.2 mol) of chlorine were passed into 15.7 g (0.1 mol) of α-thiocyano-pinacolin and 18 g (0.22 mol) of sodium acetate in 70 ml of glacial acetic acid at about 30° C. in the course of about 1 hour. The mixture was then stirred at 40° C. for a further 30 minutes, the decolorised suspension was concentrated, water was added to the residue, the mixture was extracted by shaking with ethylene chloride and the organic phase was concentrated.

19 g (that is to say, 84% of theory) of α,α-dichloro-α-thiocyano-pinacolin were obtained in the form of a honey-yellow oil which crystallized on standing. After stirring the crystals with ethanol and washing and drying them, colorless crystals of melting point 52° C. were obtained.

EXAMPLE 17

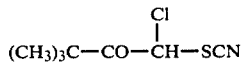
(17)

When the procedure in Example 16 was followed but only half the amount of chlorine was employed, after working up, 14.3 g (that is to say, 75% of theory) of α-chloro-α-thiocyano-pinacolin were obtained in the form of a light yellow, viscous oil.

Example 18

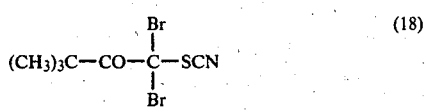

26.5 g (0.166 mol) of bromine were added dropwise to 13 g (0.083 mol) of α-thiocyano-pinacolin and 14 g (0.17 mol) of sodium acetate in 80 ml of glacial acetic acid at a temperature of 25° to 30° C. and the mixture was subsequently stirred at 40° C. for 4 hours. The yellow suspension was then stirred into 400 ml of ice-water, a few ml of sodium bisulphite solution were added in order to remove residues of bromine, the white suspension was then filtered and the residue was washed and dried. 22 g (that is to say, 84% of theory) of α,α-dibromo-α-thiocyano-pinacolin were obtained in the form of colorless crystals of melting point 75° C.

Example 19

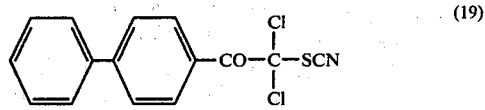

10 g (0.04 mol) of 4-phenyl-phenacyl thiocyanate and 7.9 g (0.096 mol) of sodium acetate were suspended in 100 ml of glacial acetic acid; 5.7 g (0.08 mol) of chlorine were then passed in at a temperature of 25° to 30° C. After subsequently stirring the mixture for 1.5 hours, the reaction had ended. The reaction mixture was poured into 1.8 liters of ice-water and the fine white precipitate was filtered off and dried. 11.5 g (that is to say, 89% of theory) of 4-phenyl-α,α-dichlorophenacyl thiocyanate of melting point 106° C. were obtained.

Example 20

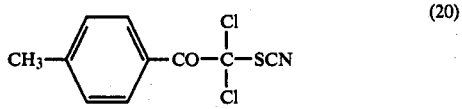

Melting point 57° C.

The compound was prepared in accordance with the compounds described above.

Example 21

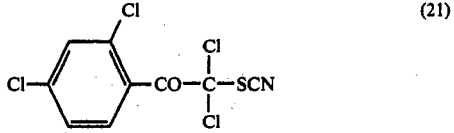

Melting point 48° C.

The compound was prepared in accordance with the compounds described above.

The bactericidal activity of the compound of this invention is illustrated by the following examples wherein the compounds according to the present invention are each identified by the number (given in brackets) from the preparative examples hereinabove.

The known comparison compound (A) is copper oxychloride, 3 Cu(OH)$_2$·CuCl$_2$ ·xH$_2$O.

Example 22

Agar plate test

Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate Composition of the solvent mixture:
0.19 part by weight of acetone or dimethylformamide
0.01 part by weight of emulsifier (alkylaryl polyglycol ether)
1.80 parts by weight of water Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg.C.) and was then poured into Petri dishes of 9 cm diameter. Control plates to which the preparation had not been added were also set up.

When the nutrient medium had cooled and solidified, the plates were inoculated with the species of organisms stated hereinbelow and incubated at about 22 deg.C.

The species of bacteria used as the organisms in the test were *Erwinia carotovora, Erwinia mangiferae, Pseudomonas lachrymans, Xanthomonas pelargonii, Xanthomonas vesicatoria, Xanthomonas malvacearum* and *Xanthomonas campestris.*

Evaluation was carried out after 2–4 days, dependent upon the speed of growth of the organisms. When evaluation was carried out the radial growth of the organism on the treated nutrient media was compared with the growth on the control nutrient medium. In the evaluation of the organism growth, the following characteristic values were used:
1 no growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

TABLE 1

| | | Agar plate test | | | | | | |
|---|---|---|---|---|---|---|---|---|
| | | Bacteria | | | | | | |
| Active compound | Concentration [ppm] | Erwinia carotovora | Erwinia mangiferae | Pseudomonas lachrymans | Xanthomonas pelargonii | Xanthomonas vesicatoria | Xanthomonas malvacearum | Xanthomonas campestris |
| (A) | 25 | 7 | 9 | 9 | 9 | 9 | 9 | 9 |

TABLE 1-continued

| Active compound | Concentration [ppm] | Agar plate test / Bacteria: *Erwinia carotovora* | *Erwinia mangiferae* | *Pseudomonas lachrymans* | *Xanthomonas pelargonii* | *Xanthomonas vesicatoria* | *Xanthomonas malvacearum* | *Xanthomonas campestris* |
|---|---|---|---|---|---|---|---|---|
| (1) | 25 | 1 | 1 | 3 | 1 | 1 | 1 | 1 |
| (7) | 25 | 1 | 1 | 3 | 1 | 1 | 1 | 1 |
| (12) | 25 | 1 | 1 | 3 | 1 | 1 | 1 | 1 |
| (9) | 25 | 1 | 1 | 1 | 1 | 1 | 1 | 1 |
| (20) | 25 | 1 | 1 | 3 | 1 | 1 | 1 | 1 |
| (14) | 25 | 1 | 1 | 3 | 1 | 1 | 1 | 1 |
| (8) | 25 | 1 | 1 | 1 | 1 | 1 | 1 | 1 |
| (11) | 25 | 1 | 1 | 3 | 1 | 1 | 1 | 1 |
| (19) | 25 | 1 | 1 | 3 | 1 | 1 | 2 | 1 |

Example 23

Bacteria test/Xanthomonas oryzae

Solvent: 11.75 parts by weight of acetone Dispersing agent: 0.75 part by weight of alkylaryl polyglycol ether Water: 987.50 parts by weight The amount of active compound required for the desired active compound concentration in the spray liquor was mixed with the stated amount of the solvent and of the dispersing agent and the concentrate was diluted with the stated amount of water.

30 rice plants which were about 40 days old were sprayed with the spray liquor until dripping wet. The plants remained in a greenhouse, at temperatures of 22 to 24 deg.C. and a relative atmospheric humidity of about 70%, until they had dried. Needles were then dipped into an aqueous bacterial suspension of *Xanthomonas oryzae* and the plants were inoculated by pricking the leaves. After the inoculation, the leaves stood for 24 hours at 100% relative atmospheric humidity and thereafter in a room at 26 to 28 deg.C. and 80% relative atmospheric humidity.

10 days after the inoculation, the infection of all pricked inoculated leaves of plants which had beforehand been treated with the preparation was evaluated, using a scale of from 1 to 9. 1 denoted 100% action, 3 denoted a good action, 5 denoted a moderate action and 9 denoted no action.

The active compounds, active compound concentrations and results can be seen from the table which follows:

TABLE 2

| Active compound | Bacteria test/*Xanthomonas oryzae*: Infection at an active compound concentration of 0.025% by weight |
|---|---|
| (A) | 7 |
| (7) | 3 |
| (12) | 5 |
| (9) | 5 |
| (20) | 5 |
| (14) | 3 |
| (21) | 3 |

It will be appreciated that the instant specification and examples are set forth by way of illustration and not limitation, and that various modifications and changes may be made without departing from the spirit and scope of the present invention.

What is claimed is:

1. A method of combating phytopathogenic bacteria comprising applying to plants or seeds an acylhalogenomethyl thiocyanate of the formula in which R is alkyl with up to 6 carbon atoms, thienyl, phenyl, naphthyl, or phenyl substituted by halogen, hydroxy, alkyl with 1 to 4 carbon atoms, alkoxy with up to 4 carbon atoms, nitro or phenyl, X is halogen, Y is halogen or hydrogen, the compound being applied in an amount effective to combat said bacteria but not substantially to affect plants or seed.

2. A method according to claim 1, in which

R is alkyl with 1 to 4 carbon atoms, thienyl, phenyl, naphthyl, or phenyl substituted by alkyl with 1 to 4 carbon atoms, methoxy, hydroxy, chlorine, bromine, nitro or phenyl, X is chlorine or bromine, and Y is chlorine, bromine or hydrogen.

3. The method according to claim 1, wherein such compound is 3,4-dichloro-α,α-dichlorophenacyl thiocyanate of the formula 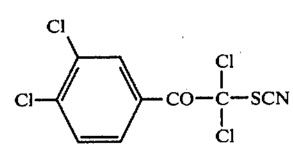 4. The method according to claim 1, wherein such compound is 4-methoxy-α,α-dichlorophenacyl thiocyanate of the formula 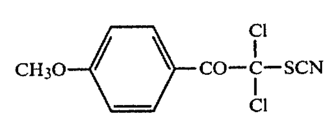 5. The method according to claim 1, wherein such compound is thiocyano-dichloromethyl-β-naphthyl ketone of the formula 6. The method according to claim 1, wherein such compound is 4-methyl-α,α-dichlorophenacyl thiocyanate of the formula
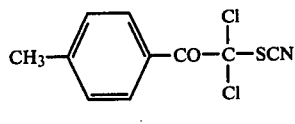
7. The method according to claim 1, wherein such compound is 2,4-dichloro-α,α-dichlorophenacyl thiocyanate of the formula
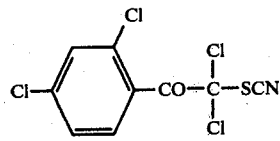
8. The method according to claim 1, in which the active compound is applied to seed in an amount of about 0.001 to 50 g per kg of seed.
* * * * *